United States Patent [19]

Aubert et al.

[11] Patent Number: 4,670,781
[45] Date of Patent: Jun. 2, 1987

[54] PROCESS AND INSTALLATION FOR THE APPRECIATION OF VARIATIONS IN TIME OF CHARACTERISTICS OF A ZONE OF OR THE WHOLE OF A PERSON

[75] Inventors: Lucien Aubert, Cap D'Ail; Philippe Anthoine, Nice; Pierre A. Corcuff, Neuilly sur Marne, all of France

[73] Assignee: L'Oreal, Paris, France

[21] Appl. No.: 739,173

[22] Filed: May 30, 1985

[30] Foreign Application Priority Data

Jun. 6, 1984 [FR] France ............................ 84 08854

[51] Int. Cl.$^4$ ............................................ H04N 7/18
[52] U.S. Cl. ...................................... 358/93; 358/107; 128/774
[58] Field of Search ............... 358/93, 107, 903, 96, 358/183; 356/376, 386, 387; 128/774

[56] References Cited

U.S. PATENT DOCUMENTS

| 4,387,392 | 6/1983 | Grattoni | 358/96 |
| 4,406,544 | 9/1983 | Takada | 356/387 |
| 4,486,774 | 12/1984 | Maloomian | 358/93 |
| 4,539,585 | 9/1985 | Spackova | 358/93 |
| 4,602,280 | 7/1986 | Maloomian | 358/183 |

FOREIGN PATENT DOCUMENTS

| 0062941 | 10/1982 | European Pat. Off. |
| 0119660 | 9/1984 | European Pat. Off. |
| 1211962 | 10/1959 | France |
| 1564781 | 3/1969 | France |
| 2498441 | 7/1982 | France |
| WO81/03418 | 12/1981 | PCT Int'l Appl. |
| 692923 | 6/1953 | United Kingdom |

OTHER PUBLICATIONS

IEEE—Transactions on Biomedical Engineering, vol. BME-19, No. 5, Sep. 1972, pp. 376–381—"Video-Dimension Analyzer", Yin et al.

Primary Examiner—Howard W. Britton
Attorney, Agent, or Firm—Cushman, Darby & Cushman

[57] ABSTRACT

The process permits appreciation of variations in time of characteristics, particularly dimensions or coloration or other characteristics, of a zone of or the whole of a person. Use is made of a video camera to take an image at a given moment in time of the zone of or the whole of the person; this image is recorded in an image analyzer in order to store it; at a later time the original image is recalled and, with the aid of this recalled image, the person is placed in a position as close as possible to the position occupied when the image was made at the first moment in time, a second image is taken at the later time of the zone of or the whole of the person with the aid of the video camera, and these images are measured in the image analyzer.

10 Claims, 5 Drawing Figures

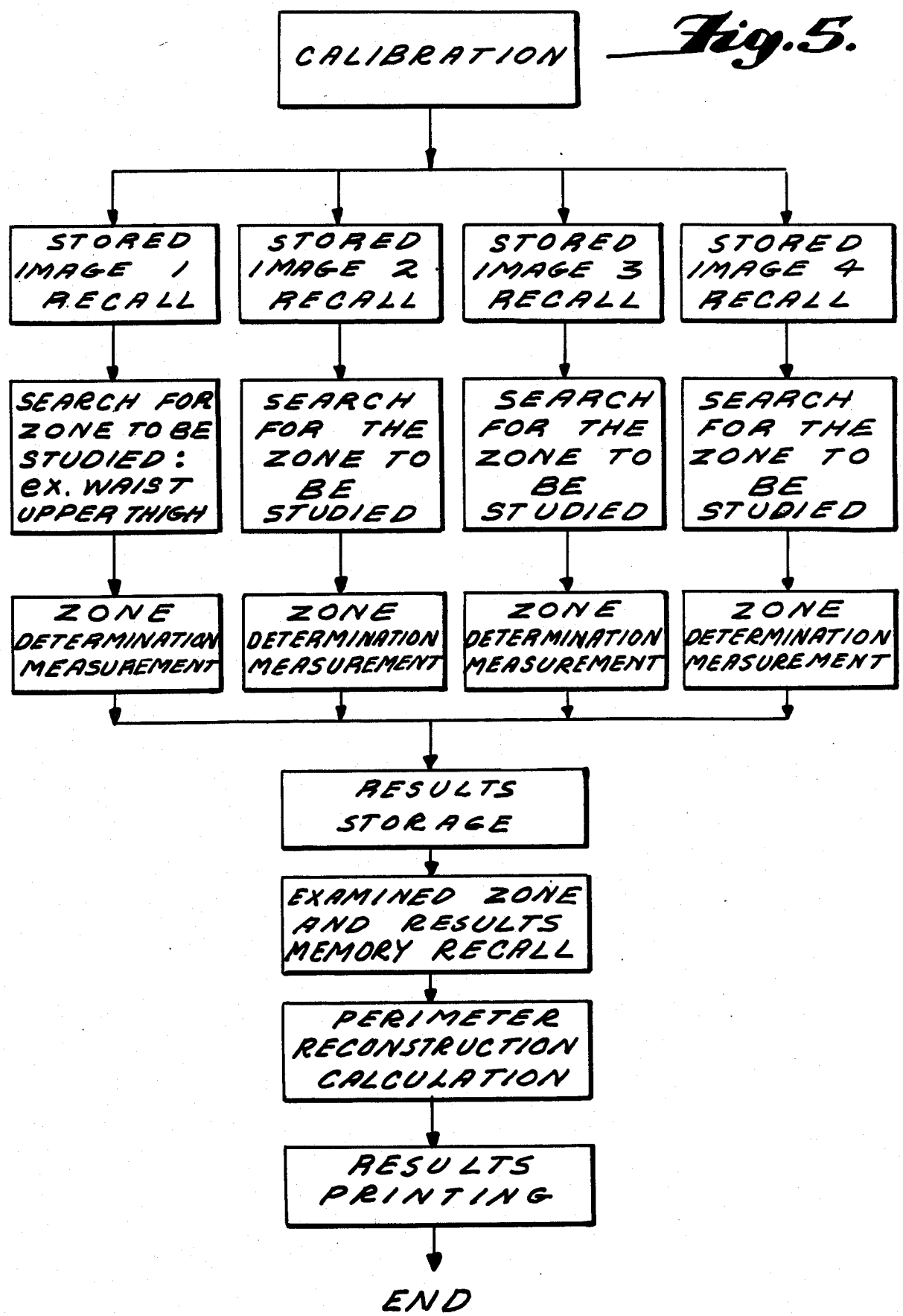

PROCESS AND INSTALLATION FOR THE APPRECIATION OF VARIATIONS IN TIME OF CHARACTERISTICS OF A ZONE OF OR THE WHOLE OF A PERSON

FIELD OF THE INVENTION

This invention relates to a process for appreciation of variations with respect to time of characteristics, particularly dimensions or coloration or other characteristics, of a zone of or the whole of a person.

A particular problem of making such an appreciation of dimensional characteristics arises when following up the effects of slimming products, or of treatments intended to modify the figure of a person.

PRIOR ART

The dimensions of the periphery of certain zones are for example measured directly. A direct measurement may sometimes also be made of folds of the skin. However, the accuracy of these measurements can be criticized, because they are not always made in the same position and under comparable conditions.

It has also been proposed to use echography for measuring by ultrasonic waves the distance between bone and skin and to follow the variations of this distance; it has also been proposed to use X-rays for making this measurement of distance between bone and skin. Nevertheless, these systems of measurement are cumbersome and usually can be made only in specialized establishments. Furthermore, in this case again the comparison of measurements made at different times does not always make it possible to appreciate accurately the possible variations. The results of each measurement depend in fact on the place where the measurement is taken and the conditions under which this measurement is made; this place and these conditions vary from one measurement to another to such an extent that the uncertainty due to positioning are of the same order of magnitude as the accuracy of the measurement itself.

This problem of appreciation of the variations of characteristics over a prolonged time is not limited to the appreciation of dimensional characteristics. It arises, for example, in aesthetics, when studying solar filters and their influence on the evolution of the coloration of zones of the body of a person.

OBJECT OF THE INVENTION

The invention seeks above all to provide a process of the type defined above which will comply better than hitherto with various practical requirements and which will in particular make it possible to make more simply and quickly and with improved accuracy, an appreciation of the variations in time of the characteristics of a zone or the whole of a person.

SUMMARY OF THE INVENTION

According to the invention there is provided a process for appreciation of variations in time of characteristics of a zone of or the whole of a person, comprising at a first time taking a first image of the zone or of the whole of the person using a video camera; recording said first image in an image analyzer for storage; later recalling the first image and, with the aid of the recalled first image placing the person in a position as close as possible to that occupied when the first image was taken; taking a second image of the zone or the whole of the person at the later time with the aid of the or a video camera; and measuring the first and second images using the image analyzer.

In the case of the whole of a person, the person may be lit in such a manner as to show up as a shadow in relation to a screen; four images are advantageously taken, namely a frontal image, a back image, and two profile images.

The invention also relates to apparatus for use in the appreciation of variations in time of a zone of or the whole of a person, is constituted by a turntable having one or more reference marks for the position of the person which is intended to stand on the turntable; a video camera having a fixed position relative to said turntable; a screen also having a fixed position relative to the turntable; and an image analyzer associated with the video camera for recording, storing and measurement of the first and second images.

Preferably, the apparatus further includes lighting means disposed on each side of the screen the light emitted by these lighting means being directed towards the surface of the screen and being diffused and reflected forwards by the screen in such a manner that a person situated in front of the screen will appear as a shadow in relation to the screen.

A First application of the process is to the appreciation of the effects of a treatment, particularly on zones such as the face, the thighs or the breasts.

Another application relates to the appreciation of the variations of coloration of a zone of the surface of a person's skin.

Another application relates to the appreciation of the evolution of cicatrices, particularly in the case of persons suffering from burns.

Another application relates to the appreciation of the evolution of weals, this appreciation being made both in respect of dimensions and in respect of coloration.

BRIEF DESCRIPTION OF THE DRAWINGS

In addition to the features explained above, the invention also comprises certain other features which will become more apparent by studying a particular embodiment which will be described with reference to the accompanying drawings but which does not in any way constitute a limitation.

FIG. 5 is finally a simplified flowchart summarizing the stages of calcuation of the perimeter of a section.

DESCRIPTION OF THE PREFERRED EMBODIMENTS

Figure 1:
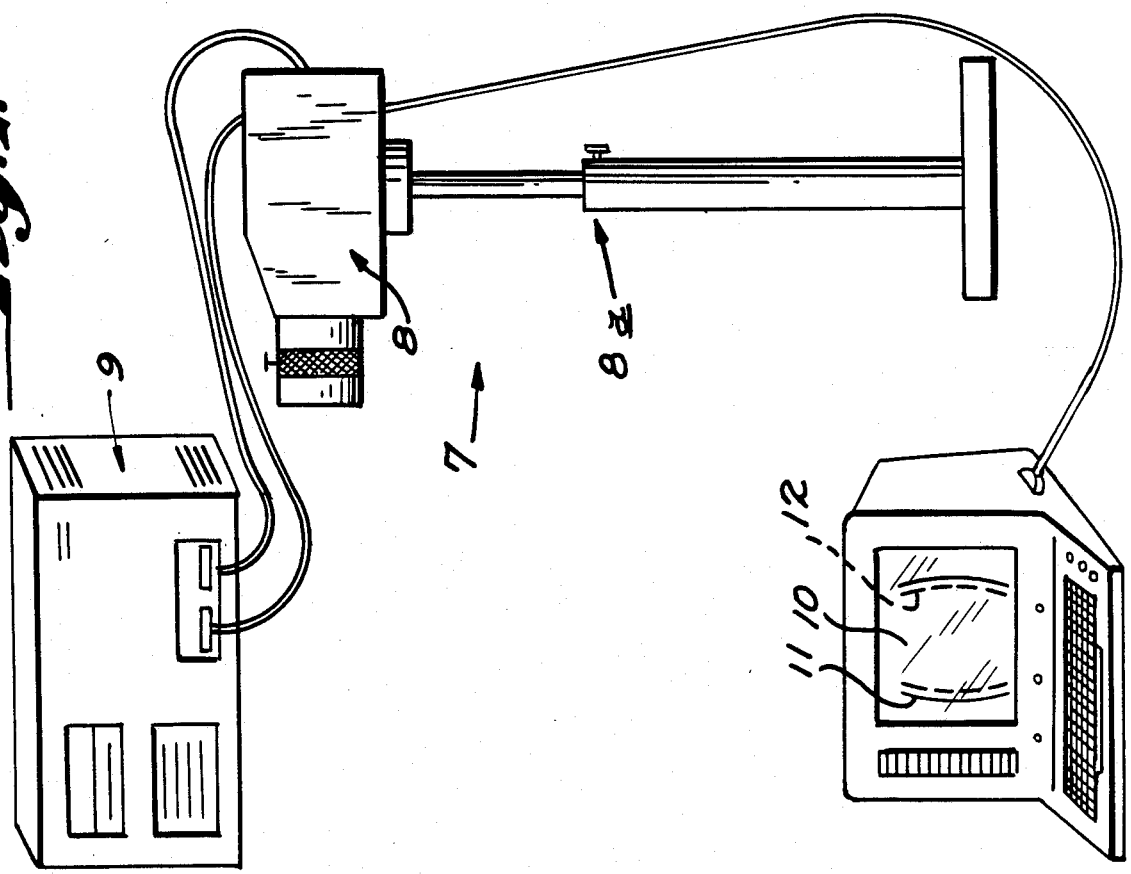
FIG. 1 of these drawings illustrates diagrammatically an installation for applying a process according to the invention.
Figure 1:
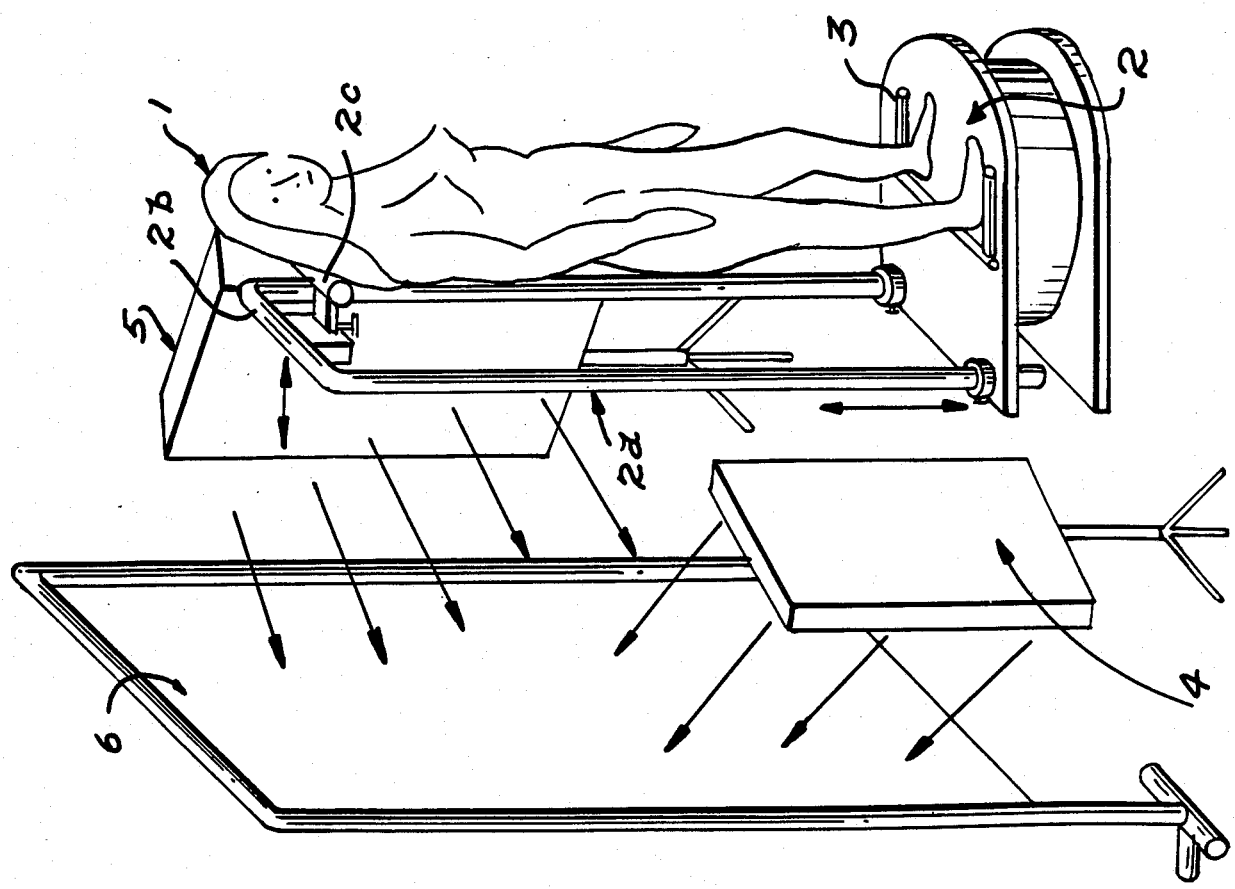

Referring to FIG. 1 of the drawings a person 1 can be seen who is standing on a turntable 2 whose mean plane is horizontal and which is adapted to turn about a vertical axis passing through its centre. This turntable 2 is provided with reference marks, formed for example by outlines 3 for the positioning of the feet of the person 1. The turntable 2 is in addition equipped at the rear with a kind of gantry 2a which is adjustable in height as indicated by the double arrow h. This gantry 2a has a top horizontal crossbar 2b, on which is mounted a support 2c, particularly a neckrest which is adjustable in a direction at right angles to the mean plane of the gantry 2a, as indicated by the double arrow l. The two uprights of the gantry 2a are parallel and sufficiently far apart not to obstruct the taking of a view of the person 1.

Lighting means 4, 5 are provided on each side of a screen 6 the emitted light being directed onto the surface of the screen. The light is diffused and reflected forwards by the screen 6, that is to say towards the right in the drawing. The person 1 is situated in front of the screen 6, which is usually white.

For an observer or an image recording apparatus 7 situated still further forward than the person 1 in relation to the screen 6 (the person therefore being situated between the screen 6 and the camera 7) and turned towards the screen 6, the person 1 will appear as a shadow or dark silhouette in relation to the screen 6, which forms a light background.

The image recording apparatus 7 comprises at least one video camera 8 which is in a fixed position relative to the turntable 2 and the screen 6. Support means 8a are adapted to hold this camera 8 in a fixed position. These support means 8a are so arranged as to permit adjustment of the height and direction of the camera 8, which is then locked in the adjusted position. The screen 6 is held in a fixed position relative to the turntable 2 and also the lighting means 4, 5.

The video camera 8 is connected to means for storing or recording the images. These means consist of an image analyzer 9, for example of the type available from Cambridge Instruments under the designation QTM 900. This image analysis system includes calculation means (particularly a computer) and has automatic facilities for data acquisition, storage, memory recall, handling and display of images of different origins for the recognition, modification and measurement of the particles contained in these images. It permits identification of these particles by combination of densitometric measurements of size and shape. The images detected on the grey scale (64 grey values) are converted into binary images and stored.

The system makes it possible to display on a video screen 10 two binary images simultaneously superposed, and to distinguish from the original image any details added or removed without loss of details in the original image. FIG. 1 shows diagrammatically a part of the contours 11 (solid lines) and 12 (broken lines) of two superposed images.

At a given moment of time T an image is taken, with the aid of the camera 8, of a zone of or the whole of the person 1. For example an image is taken of a zone of the person between the waist and the knees; this zone forms a silhouette contrasting against the screen 6 as a shadow.

At a subsequent moment $T+\Delta T$ (th expression $\Delta T$ corresponding to several days weeks or even several months), the original image (taken at the moment T) is recalled, this being a binary image stored by the measuring system, and displayed on the control screen of the image analyzer 9. This being the case, when at the moment $T+\Delta T$ this binary image is recalled, the person 1 can be placed in a position as close as possible to that occupied at the first moment of time T. The second "living" image, which appears in real time on the screen 10, and the first stored image, recalled to the screen 10, are so to speak superposed. There is therefore a kind of self-positioning of the person 1, which makes it possible to reduce considerably the sources of inaccuracies previously mentioned, which occur in a comparison made at different intervals of time.

The second image in grey form, obtained at the moment $T+\Delta T$, is also converted into a binary image and stored. The recall of the two images (taken at the moments T and $T+\Delta T$) and their superposition on the screen of the analyzer 9 permit direct appreciation of variations, such as the difference between contours. The zones of difference which can be photographed can appear as hatched areas on the screen of the apparatus, these differences being calculated quantitatively by the computer.

At another later moment it will therefore be possible to make a further comparison with the images taken at previous times.

The turntable 2 can, for example, be placed in four successive different angular positions offset by 90° relative to one another, so that at a given moment it is possible to obtain four images of the person 1 corresponding to four positions: a frontal view, a rear view, and two profile views.

The process can be applied to the study of particular zones of the person 1, such as the face, thighs or breasts. The appreciations of variations in particular the measurements need not relate to dimensional characteristics but to the coloration of a region of the skin (appreciation of erythema, of the effectiveness of solar filters, and so on). In this case use is made of direct images of the person 1 without using a shadow silhouette on the screen 6. The images can be observed on a video screen.

It is also possible to make use of the process for following the evolution of cicatrices, particularly in the case of persons who have suffered burns, or the evolution of weals, in which case the appreciation will relate both to dimensions (area) and to colour.

The process and the installation according to the invention are of particular interest for following the evolution of the figure of a person undergoing slimming treatment or using slimming products.

More precisely a three-dimensional analysis is made with the aid of the four measurements indicated above.

Figure 2:
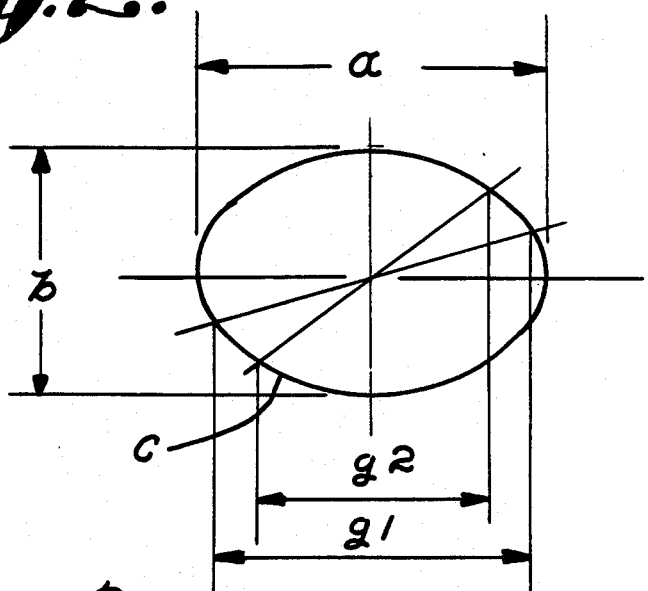
FIG. 2 is a diagram illustrating the determination of the axes of the section of a zone.

For example if a fictitious cross-section C (FIG. 2) of a thigh at a given height is considered, it may be regarded as substantially elliptical. The two front and back measurements will make it possible to determine by taking their mean, the major axis a of this cross-section: the two profile measurements make it possible, by taking their mean, to determine the minor axis b of this section C, at right angles to the axis a.

A calculation program is provided to enable the computer to calculate the length of the perimeter of the cross-section C.

The same method can be applied to a cross-section at any level. Instead of making measurements offset angularly by 90°, it would be possible to make more numerous measurements, for example offset successively by 10°, by suitably turning the turntable 2. The distances such as g1, g2... shown in FIG. 2 would be determined in succession, thus making it possible to calculate more accurately the perimeter C, by determining a larger number of points on this perimeter.

The quantification achieved with the apparatus of the invention is particularly precise because the zone generally studied, situated between the waist and the knee, is split up into 700 lines.

Qualitative variations (location of places where variations in perimeter occur) are quickly appreciated and recorded.

Series of measurements made with the apparatus of the invention have made it possible to establish that the accuracy of measurement of the perimeter C is of the order of 1 mm. These measurements have excellent correlation with clinical tests (measurements made with a tape-measure).

Series of measurements, such as those mentioned, have made it possible to test the effectiveness of a slimming product after application of the product for 10 days and 20 days.

The silhouette of the subject, contrasting against the white background, is recorded in the four positions (right and left profiles, front and back) at the time To, and this recording is then repeated under the same conditions after application of the product for 10 days and then for 20 days. The image is stored in the central store of the image analyzer 9 and can thus be recalled for the second and third examinations for superposition and comparison of the silhouettes.

On the one hand, the results are expressed in qualitative form: the difference observed between the silhouettes at the time To and 10 and 20 days thereafter can be displayed direct on the control screen 10 and photographed. In diagrammatical form, in FIG. 1, the solid line 11 represents a part of the contour of the silhouette at the time To, and the broken line 12 represents the contour of this silhouette, For example, after treatment for 20 days.

On the other hand, the results are expressed in quantitative form. Each silhouette at the time To, and 10 and 20 days later, can be measured to within 1 millimeter and processed mathematically.

Based on the diameter recorded for each zone (hips, upper thighs, mid-thighs), the mean perimeter is calculated, taking into account the mean diameter measured in the four positions (right and left) profiles, back and front).

Figure 3:
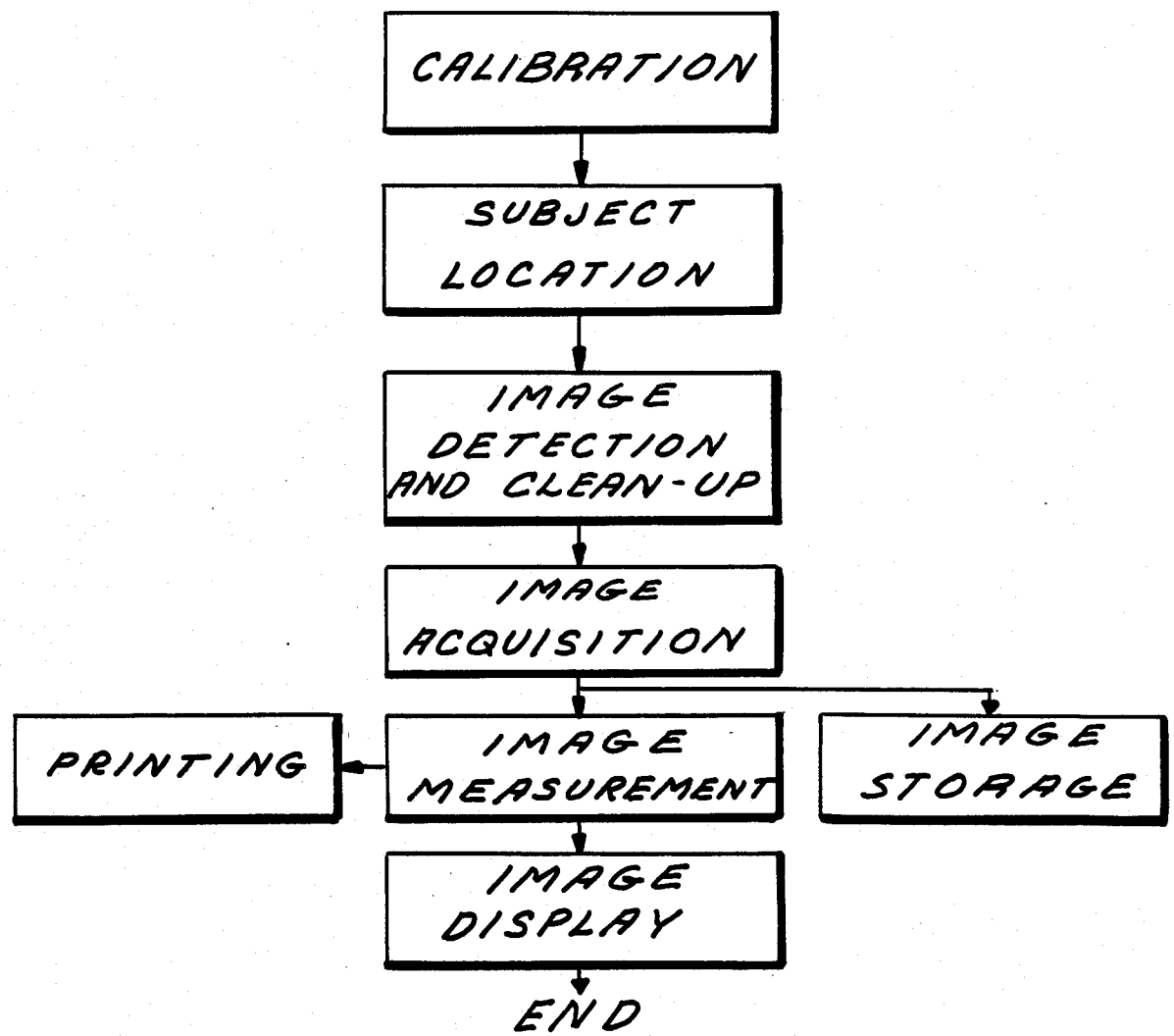
FIG. 3 is a simplified flowchart summarizing the stages of acquisition and measurement of an image.

Referring to FIG. 3, it is possible to follow schematically the steps of image acquisition and measurement according to the invention with the aid of a program input into the computer for the purpose.

In a first stage, known as "calibration", the system is adjusted, in particular to permit good correspondence between the dimensions on the image and the real dimensions.

A second "subject location" has the aim of positioning the image on the screen.

A third "image detection and clean-up" stage makes it possible to detect the image and eliminate any aberration points of the image, due for example to parasites (ghosting).

The fourth "image acquisition" stage consists of an analysis of the image by scanning and determination of the coordinates of points of the image.

The image is then measured ("image measurement") and stored ("image storage").

The image is displayed on the screen ("image display") and a "print" stage may be provided to produce the image in printed form.

Figure 4:
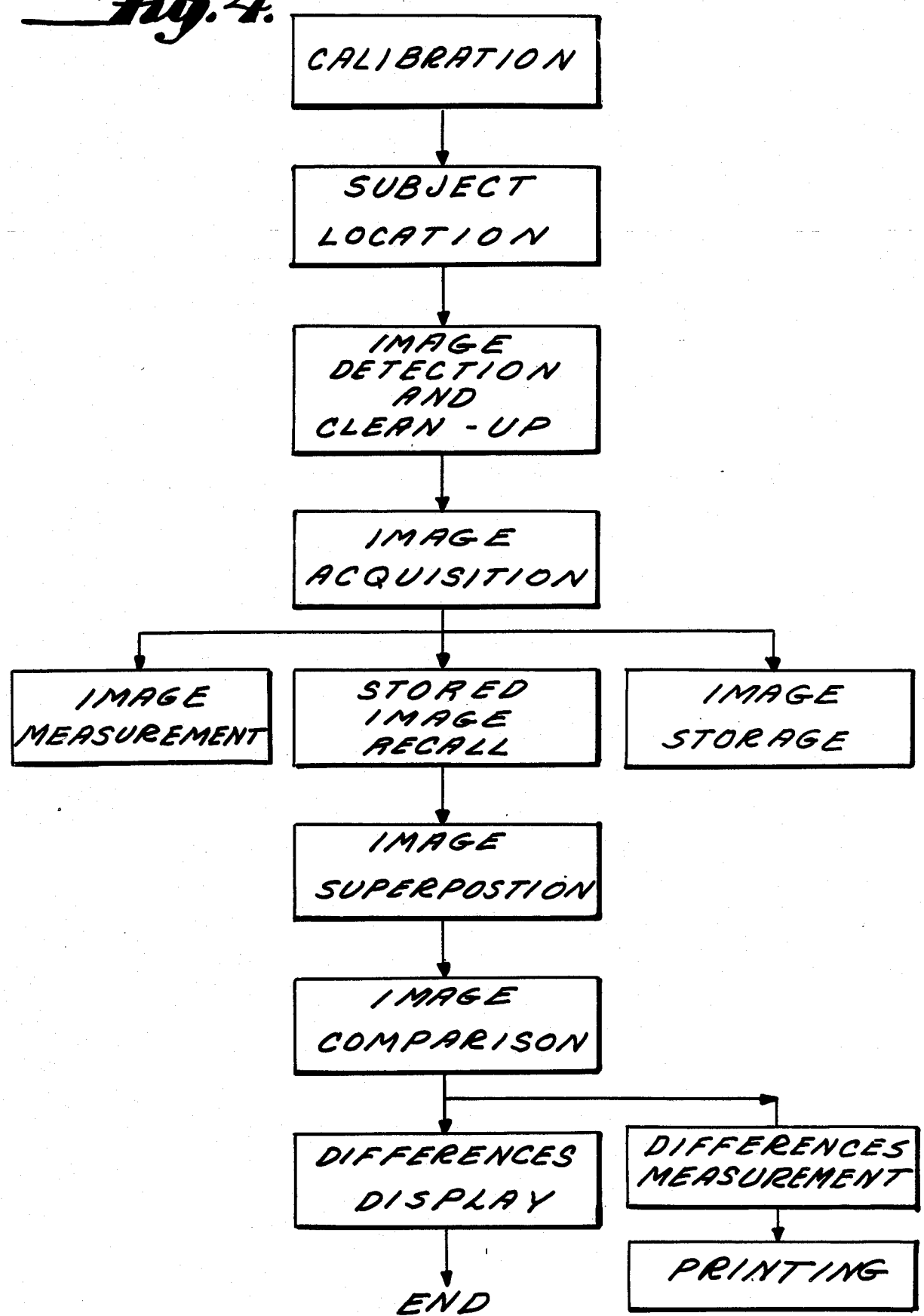
FIG. 4 is a simplified flowchart summarizing the stages of comparison of two images and measurement of their differences.

FIG. 4 makes it possible to follow schematically the stages of comparison of two images at the moment of time T+ΔT, a first image having been stored at the moment T. For the second image taken at the time T+ΔT the first stages shown in FIG. 3 are repeated, and these will not be discussed again. After acquisition of the image (the second image), a "stored image recall" is made, followed by superposition of this first recalled image and the image being taken at that moment ("image superposition" stage).

Then "image comparison", "differences display", and "differences measurement" will occur, optionally followed by "printing" of the results of measurements.

FIG. 5 summarises the stages of calculation of the perimeter of a section.

After the adjustment ("calibration") stage, the four images (front, back, two profiles) of the person are recalled.

In each image a search is made for the zone to be studied (for example, waist, upper thigh, and so on). The zone is then measured ("zone determination measurement"). The results of the measurements are stored.

The results stored are then recalled ("examined zone and results memory recall") whereupon the perimeter is calculated ("perimeter reconstruction calculation") and the results of the calculation are printed.

We claim:

1. A process for the appreciation of variations in time of characteristics of a zone of or the whole of a person, comprising at a given moment of time using a video camera to take at least one first image of the zone or of the whole of the person; recording this at least one first image in an image analyzer for storage; at a later time recalling the said at least one first image and, with the aid of the recalled image, placing the person in a position as close as possible to that occupied when said at least one first image was taken; later taking at least one second image of the zone or of the whole of the person with the aid of a video camera; and measuring said first and second images in the image analyzer, with superposition of said images on the screen of the analyzer so as to permit direct appreciation of said variations including a difference between contours.

2. A process according to claim 1, further comprising the steps of placing the person in front of a screen, and lighting the screen by a lighting system in such a manner that the whole of the person appears as a shadow in relation to the screen.

3. A process according to claim 1, comprising taking a set of first images at said given time and taking a set of second images at said later time, the first and second images each comprising images from different directions.

4. A process according to claim 3, wherein each set of images comprises four images of the person, corresponding to a frontal image, a back image, and two profile images.

5. A process according to claim 3, comprising determining two orthogonal axes of a given cross-section of a zone of the body with the aid of said sets of images, and calculating the perimeter of the cross-section.

6. A process according to claim 1, and comprising taking at least one further image later than said second images and measuring said at least one further image with the first and second images using the image analyser.

7. A process according to claim 1, and further comprising the step of subjecting the zone or the whole of the body to a treatment, between the taking of said at least one first image and said at least one second image.

8. A process according to claim 1, wherein the characteristic whose variations are being appreciated is the coloration of a zone of the surface of the skin of a person.

9. A process according to claim 1, wherein the appreciation is in respect of the evolution of cicatrices.

10. A process according to claim 1, wherein the appreciation is in respect of the evolution of weals, both in respect of dimension and of coloration of said weals.

* * * * *